United States Patent [19]

Takashio et al.

[11] Patent Number: 4,753,882

[45] Date of Patent: Jun. 28, 1988

[54] UREASE AND PROCESS FOR PREPARATION THEREOF

[75] Inventors: Masachika Takashio; Yasuo Yoneda; Yutaka Mitani, all of Yaizu; Takahide Chikano, Shizuoka; Minoru Kamimura, Yaizu, all of Japan

[73] Assignee: Sapporo Breweries Limited, Tokyo, Japan

[21] Appl. No.: 891,258

[22] Filed: Jul. 28, 1986

[30] Foreign Application Priority Data

Jan. 13, 1986 [JP] Japan .................................. 61-3627

[51] Int. Cl.⁴ ........................... C12N 9/80; C12R 1/07
[52] U.S. Cl. ..................................... 435/228; 435/832
[58] Field of Search ......................................... 435/228

[56] References Cited

FOREIGN PATENT DOCUMENTS 79792  5/1983  European Pat. Off. ............ 435/228
17987  1/1984  Japan ................................... 435/228

Primary Examiner—Lionel M. Shapiro
Attorney, Agent, or Firm—Frishauf, Holtz, Goodman & Woodward

[57] ABSTRACT

Different from conventional urease products, the urease of the present invention has excellent stability, and has a smaller Km value. The urease of this invention is produced microbiologically by a thermophilic microorganism belonging to the genus of Bacillus and especially named as Bacillus sp. TB-90 which is a novel species distinguishable from any of the microorganisms belonging to the genus of Bacillus.

3 Claims, 5 Drawing Sheets

UREASE AND PROCESS FOR PREPARATION THEREOF

BACKGROUND OF THE INVENTION

The present invention relates to novel urease and a process for the preparation thereof. Urease is used for the quantitative determination of urea and in artificial kidneys. The present invention is intended to prepare urease having suitable properties for the above purposes using thermophilic microorganisms.

Urease (EC 3.5.1.5) is an enzyme catalyzing decomposition of urea which results in the formation of ammonia and carbon dioxide and can be widely detected in plants, animals, microorganisms and so forth.

Urease derived from a jack bean and urease derived from microorganisms (see Japanese Patent Kokai Koho Nos. 86081/1983 and 17987/1984) have already been prepared on commercial scale and utilized in a clinical test reagent, an artifical kidney apparatus and so forth.

These known ureases, however, have a disadvantage of being ultimately unstable. In order to overcome this disadvantage of unstability, various methods have already been proposed.

Japanese Patent Kokai Koho No. 117488/1977, for example, discloses a method in which glutathione, ethylenediaminetetraacetic acid (EDTA) and citric acid salts are used in combination with urease. Japanese Patent Kokai Koho No. 138389/1972 discloses a method in which a thiol compound, a chelate reagent and an organic dibasic acid or its salt are used in combination with urease; Japanese Patent Kokai Koho No. 28498/1984, a method in which polyvinyl alcohol, N-acetylcystene and EDTA are used in combination with urease; and Japanese Patent Kokai Koho No. 82318/1984, a method in which in addition to the above substances, disaccharide is further used in combination. These methods, however, fail to sufficiently improve the stability of urease.

Enzymes derived from thermophilic microorganisms are generally considered to have advantages in that the stability is satisfactorily high and the cultivation period for the enzyme production is rather short. It has not yet been reported that urease can be successfully prepared using thermophilic microorganisms.

SUMMARY OF THE INVENTION

An object of the present invention provides urease having high stability.

Another object of the present invention provides a process for preparing urease having high stability by culturing thermophilic microorganisms.

As a result of extensive investigations, it has been found that a strain TB-90 belonging to the genus Bacillus (hereinafter abbreviated to "Strain TB-90") produces a large amount of urease of high stability in its fermentation broth.

Based on these findings, the present invention has been accomplished.

The present invention, in one embodiment thereof, relates to a urease which has an action of hydrolyzing urea and is stable at pH of 4 to 11 or at a temperature of 56° C. or less in a liquid state.

In another embodiment, the present invention relates to a process for preparing a urease which comprises cultivating a thermophilic microorganism in a nutrient medium, said microorganism belonging to the genus Bacillus and having an ability to produce a urease which has an action of hydrolyzing urea and is stable at pH of 4 to 11 or at a temperature of 56° C. or less in a liquid state, thereby forming the urease and then recovering the urease from the fermentation broth.

DETAILED DESCRIPTION OF THE INVENTION

Figure 1:
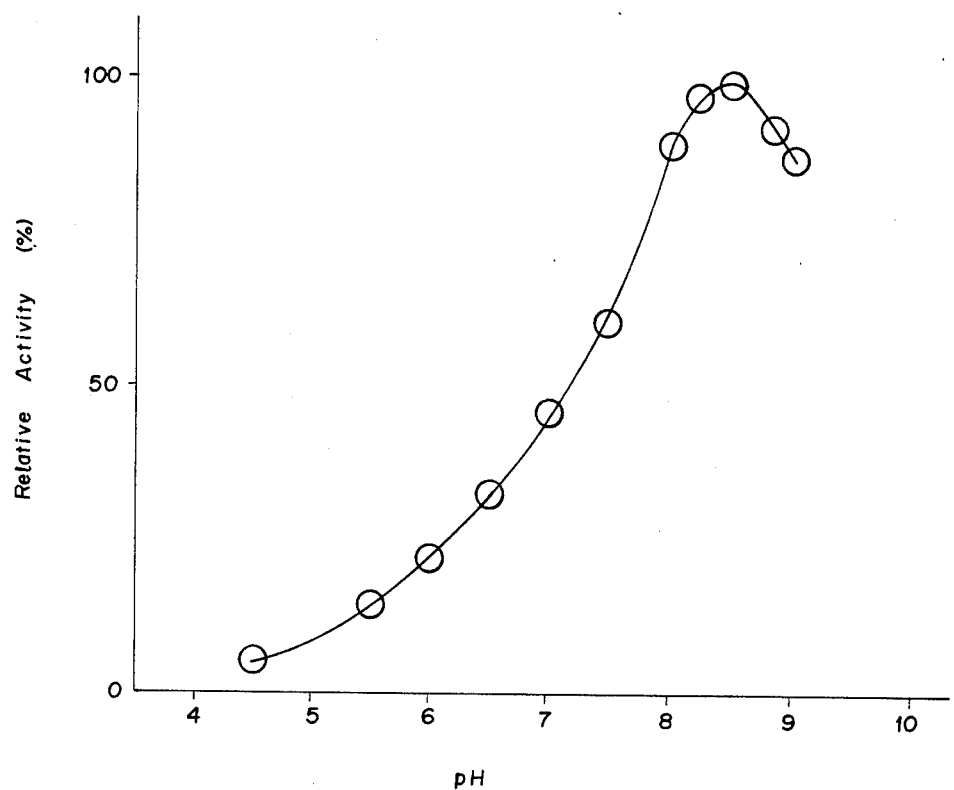
FIG. 1 is a graph showing the optimum pH of the urease of the present invention.

Strain TB-90 is the same as a strain which has been found to produce uricase (EC 1.7.3.3) by the present inventors. Thus this strain permits to produce a large amount of urease simultaneously with a fermentative production of uricase. The reason for this is considered that the metabolism route is such that uric acid is decomposed by uricase and further converted into urea and thus urease decomposing this urea is efficiently produced. Of course, the strain of the present invention can produce urease in other culture medium. For example, the strain can be grown in the ordinary medium, and addition of urea to the medium is more effective for the formation of urease.

The microorganism used in the inventive method for the microbiological production of the novel urease is not particularly limitative provided that it is a thermophilic microorganism belonging to the genus of Bacillus and capable of producing the above defined novel urease. Such a microorganism includes not only the above mentioned TB-90 but also any natural or artificial mutant strains thereof as well as various kinds of organisms into which the genes of the above mentioned bacterial strains have been transferred provided that they have an ability of producing the novel urease.

Following are the bacteriological properties by which the microorganism of TB-90 is characterized. The examination of these properties was carried out according to the procedure and using the formulation of the culture medium described in the books of "Classification and identification of microorganisms" edited by T. Hasegawa, published by Tokyo University Press and "Methods of identification of microorganisms" published by Eisei Gijutsu Kai, Japan.

[Morphological characteristics] (after 18 hours of culturing at 55° C.)

1. Shape and dimensions of cells: rods, 0.5–0.8×1.3–2 μm
2. Polymorphism: none
3. Motility: none
4. Spores: circular endogenous spores formed at the center of a cell
5. Gram reaction: positive
6. Acid-fast stain: none
7. Capsules: none
8. Metachromatic granule: none

[Cultural properties] (after 18 hours culturing at 55° C.)
1. Nutrient-agar plate culture
   Shape: circular Periphery: smooth
Elevation: flat
Luster: not strong
Surface: somewhat coarse
Color: translucent
2. Nutrient-agar slant culture
   Growth: good
   Shape: filamentous
3. Nutrient liquid culture
   Surface growth: none
   Turbidity: clear
   Precipitates: a little
   Coloration and decoloration: none
4. Nutrient-gelatin stab culture (examination of the solidified state of the medium by cooling after culturing at 55° C. for a length of time, 30% gelatin added)
   good growth with a large volume of precipitates but no liquefaction of gelatin
5. Nutrient-agar stab culture
   Shape: torous (in the vicinity of surface only)
   Surface growth: good
6. Reaction on litmus milk
   no decoloration of litmus, pH unchanged, no coagulation, no liquefaction

[Physiological properties] (after 1–2 days of culturing at 55° C.)
1. Reduction of nitrates: none
2. MR test: negative
3. V-P test: negative
4. Formation of indole: no
5. Formation of hydrogen sulfide: no
6. Hydrolysis of starch: yes
7. Utilization of citric acid: no
8. Utilization of ammonium salt: yes
9. Formation of coloring matter: no
10. Oxidase activity: yes
11. Catalase activity: yes
12. pH for growth: 4.5 to 7.5 with an optimum pH of 5.0 to 6.5
13. Temperature for growth: 38° to 62° C. with an optimum growth temperature of 50° to 60° C.
14. Growth in anaerobic culture medium: no
15. Growth in Sabouraud dextrose-agar culture medium: good
16. Growth at 55° C. in a culture medium containing 0.02% sodium azide: no
17. Growth in 0.001% lysozyme (tested at 45° C.): no
18. Deamination of phenylalanine: no
19. Tolerance against sodium chloride: growth in 3% NaCl but no growth in 5% NaCl
20. Vitamin requirement: yes
21. Decomposition of tyrosine: no

[Utilization of carbon sources]
The microorganism grows with formation of acid by assimilating D-xylose, D-glucose, D-galactose, trehalose, cellobiose and glycerin.

The microorganism does not utilize or little utilizes arabinose, mannose, fructose, maltose, sucrose, lactose, D-sorbitol, D-mannitol, starch, 2-keto-gluconate, adonitol, xylytol, methyl-D-glucoside, N-acetyl-D-glucosamine, melezitose and raffinose.

As a result of the examination undertaken according to the method of classification described in Bergey's Manual of Determinative Bacteriology, 8th edition (1974) making reference to the above mentioned bacteriological properties of the microorganism, the subject microorganism of TB-90 was identified to belong to the genus of Bacillus. Although it may be a tentative conclusion derived from the comparison with known species belonging to the genus of Bacillus that the above described TB-90 can be either of *Bacillus stearothermophilus, Bacillus coagulans* and *Bacillus brevis* in respect of the temperature range for growth, this tentative conclusion is not supported due to the lack of motility in TB-90. Moreover, TB-90 can be differentiated from *Bacillus stearothermophilus* in respect of the ability of growth in a Sabouraud dextrose agar culture medium, from *Bacillus coagulans* in respect of the inability of growth in an anaerobic agar culture medium and in the presence of 0.02% of sodium azide and from *Bacillus brevis* in respect of the production of acid from xylose, no production of alkali in a V-P culture medium and inability of decomposing casein and tyrosine. In addition, we can show another significant difference as below: TB-90 produced uricase (EC 1.7.3.3) when uric acid was added to the culturing medium, but the standard strains described below could not. The standard strains we employed were as follow, *Bacillus stearothermophilus* IAM 11001, 11002, 11003, 11004 and 12043, *Bacillus coagulans* IAM 1194 and *Bacillus brevis* IAM 1031 deposited at Institute of Applied Microbiology of Tokyo University.

As is understood from the above given description, it is a fair conclusion that TB-90 is a novel species belonging to the genus of Bacillus in respect of the non-identicalness thereof with any of the known species. Accordingly, a strain of TB-90 has been deposited at Fermentation Research Institute, Agency of Industrial Science and Technology, Japan, as FERM BP-795.

The desired urease can be prepared by cultivating a microorganism having the urease-producing ability in a nutrient medium to form the urease and then separating the urease from the fermentation broth.

As the nutrient medium which is used in the present invention, any natural or synthetic media can be used as long as they contain suitable amounts of a carbon source, a nitrogen source, inorganic materials and if necessary, essential nutrients.

Examples of the carbon source are carbohydrates such as glucose, xylose, galactose and glycerine, and uric acid. Examples of the nitrogen source are compounds such as ammonium sulfate, ammonium chloride, sodium nitrate and urea, amino acids such as glutamic acid, nitrogen-containing natural compounds such as peptide, meat extract, yeast extract, soy bean powder and fowl excrements, and uric acid. Other inorganic compounds which can be used include various phosphoric acid salts; various sulfuric acid salts such as magnesium sulfate and ferrous sulfate; various hydrochloric acid salts such as sodium chloride and potassium chloride; zeolite; kaolin and so on; they accelerate the growth of microorganisms and enzyme formation.

In addition, if necessary, essential nutrients such as biotin, thiamine, etc. can be used.

For cultivation, both the solid culture and liquid culture can be used. Industrially the aeration-agitation cultivation method (submerged culture) is most suitable.

The cultivation can be carried out at a temperature ranging between 38° and 62° C., with the temperature range of 50° to 55° C. being suitable, pH is desirably neutral or weakly acidic.

The cultivation time is usually from 6 to 20 hours although it varies depending on cultivation conditions. When the formation of urease is confirmed, and preferably the formation of urease reaches the maximum, the cultivation should be stopped.

The present enzyme is formed mainly in the cells of microorganisms; at a later stage of the cultivation, it is accumulated also in the fermentation broth.

Urease accumulated in the fermentation broth can be recovered by appropriately combining known techniques. For example, at the end of cultivation, microorganisms are separated from the fermentation broth by techniques such as centrifugal separation and then the desired urease is extracted from the microorganisms by suitable techniques. After removing insoluble components from the extract by techniques such as centrifugal separation, the cleared supernatant is treated by acid precipitation, organic solvent precipitation, salting out, dialysis and further by various chromatographic techniques such as ion exchange, gel filtration, hydrophobic chromatography, and affinity chromatography, whereupon the urease of high purity can be recovered.

The properties of the urease of the present invention are shown below. The specimen was the enzyme obtained in Example 1 as hereinafter described. The enzyme activity was determined by either of the following two methods. Measuring Methods for the enzyme activity (1) GlDH Method A reaction solution consisting of 100 millimoles (mM) of urea, 40 mM of Tris-HCl buffer (pH 8.0), 0.86 mM of α-ketoglutaric acid, 0.31 mM of NADPH and 17.2 unit per milliliter (U/ml) of glutamate dehydrogenase (GlDH) was maintained at 37° C. Then an enzyme solution to be measured was added to the reaction solution to initiate the reaction, and a rate of decrease in absorbance at 37° C., $E_{340\ nm}$, was measured. All the concentrations are indicated in their final concentrations. A rate of decrease in NADPH was calculated from the rate of decrease in absorbance $E_{340\ nm}$, and the amount of ammonia formed by the action of urease was calculated from the rate of decrease in absorbance $E_{340} nm$.

In connection with enzyme activity, an amount of the enzyme forming 2 micromoles (μmole) of ammonia per minute was defined as one unit (1 U). This definition was calculated based on experiments carried out under the conditions described in the aforementioned GlDH method.

In cases where the GlDH method could not be applied; for example, the optimum pH, the optimum temperature and the inhibitor were investigated, the amount of ammonia formed during the reaction was measured by the indophenol method as described hereinafter.

(2) Indophenol Method

The enzyme was reacted under experimental conditions as described hereinafter and the ammonia formed was measured by the indophenol method. In more detail, the method described in The Saishin-Igaku, Vol. 21, No. 3, page 622 (1966) was employed. Since there is not a linear relation between the absorbance ($E_{625\ nm}$) determined by the indophenol method and the concentration of ammonia, a calibration graph was prepared and used.

PROPERTIES OF ENZYME (1) Reaction

The enzyme forms 2 mole of ammonia, and 1 mole of carbon dioxide from 1 mole of urea while consuming 1 mole of water.

(2) Optimum pH

The concentration of urea was adjusted to 100 mM, and as the buffer, 50 mM of a phosphate buffer was used. pHs tested were shown in FIG. 1. 100 mU of the enzyme was used per 2 ml of the reaction solution.

The reaction was carried out at 37° C. for 5 minutes. The amount of ammonia formed was measured by the aforementioned indophenol method. The relative activity at each pH is shown in FIG. 1 with the maximum activity as 100.

As apparent from FIG. 1, the optimum pH of the present enzyme was in the neighborhood of 8.5.

(3) Optimum Temperature

Figure 2:
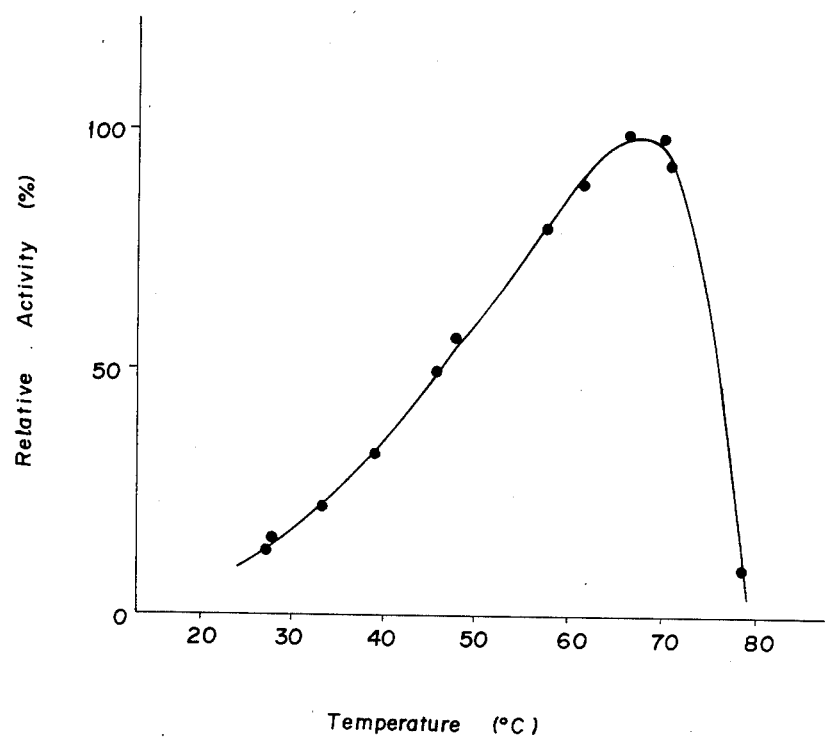
FIG. 2 is a graph showing the optimum temperature of the urease of the present invention.

The enzyme was reacted at the temperatures shown in FIG. 2 using 50 mM of a phosphate buffer (pH 7.5). The other conditions and the measuring method were the same as in the measurement of the optimum pH of (2) above.

The relative activity at each temperature is shown in FIG. 2 with the maximum activity was 100.

As apparent from FIG. 2, the optimum temperature of the present invention has been found to be in the neighborhood of 70° C.

(4) Stable pH Range

The enzyme specimen was dissolved at the concentration of 200 mU/ml in a 50 mM phosphate buffer (pH 4.5–7.0) and a 50 mM Tris-HCl buffer (pH 6.4–9.5).

Then each enzyme solution was maintained at 37° C. for 17 hours. The residual activity was measured by the aforementioned GlDH method. The relative residual activity at each pH is shown in FIG. 3 with the activity at the start of the test (i.e., prior to the treatment) as 100.

Figure 3:
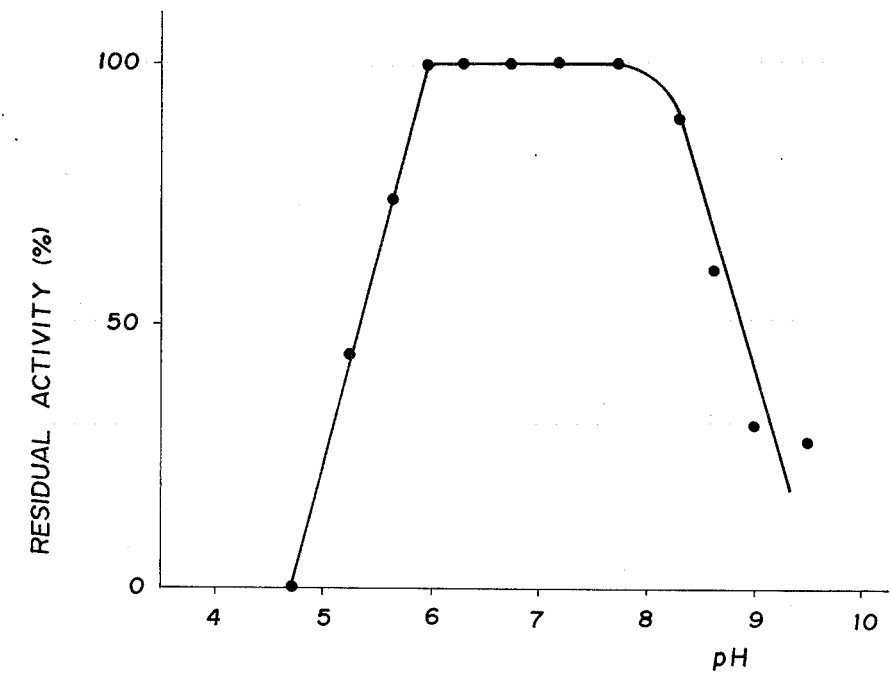
FIG. 3 is a graph showing a stable pH range of the urease of the present invention.

As apparent from FIG. 3, the present enzyme maintained its full activity in a buffer having a pH of from 5.8 to 8.0. As a control, commercially available urease derived from a jack bean was tested in the same manner as above. It was found that the activity was completely lost at every pH. Thus the usefullness of the present enzyme was clearly demonstrated.

(5) Stable Temperature Range

Figure 4:
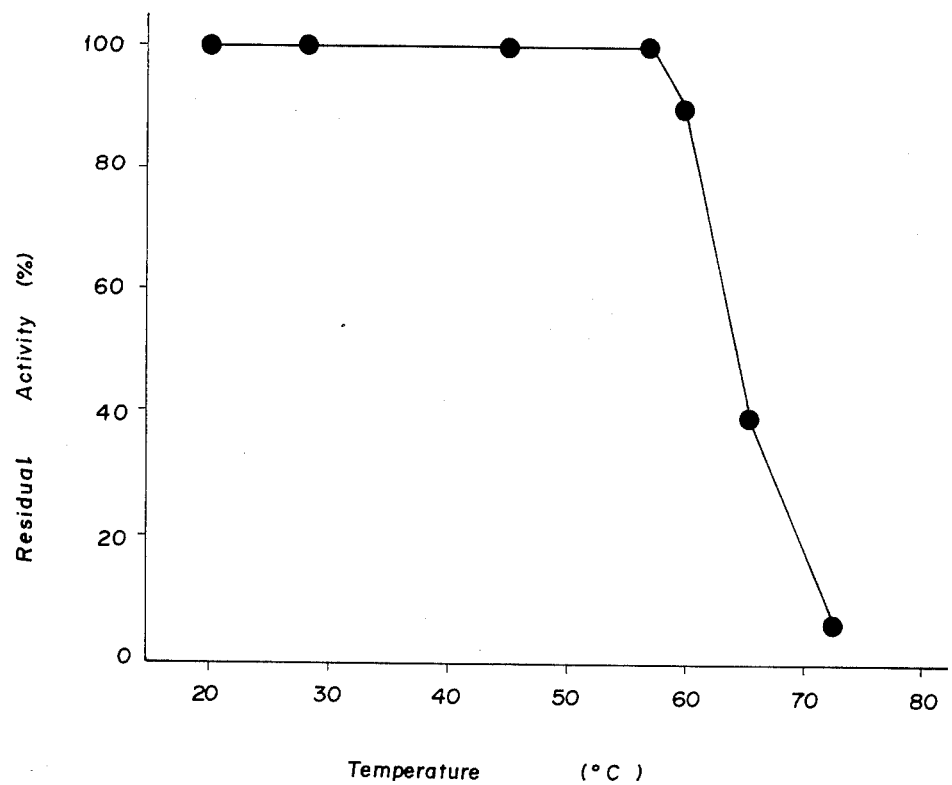
FIG. 4 is a graph showing a stable temperature range of the urease of the present invention.

The enzyme specimen was dissolved in a 50 mM phosphate buffer in a concentration of 200 mU/ml, maintained for 15 hours at each temperature as shown in FIG. 4, and then the residual activity was measured by the aforementioned GlDH method.

The residual activity at each temperature is shown in FIG. 4 with the activity at the start of the test (i.e., prior to treatment) as 100. The present enzyme maintained its full activity when treated at a temperature of not more than about 50° C.

(6) Storage Stability

Figure 5:
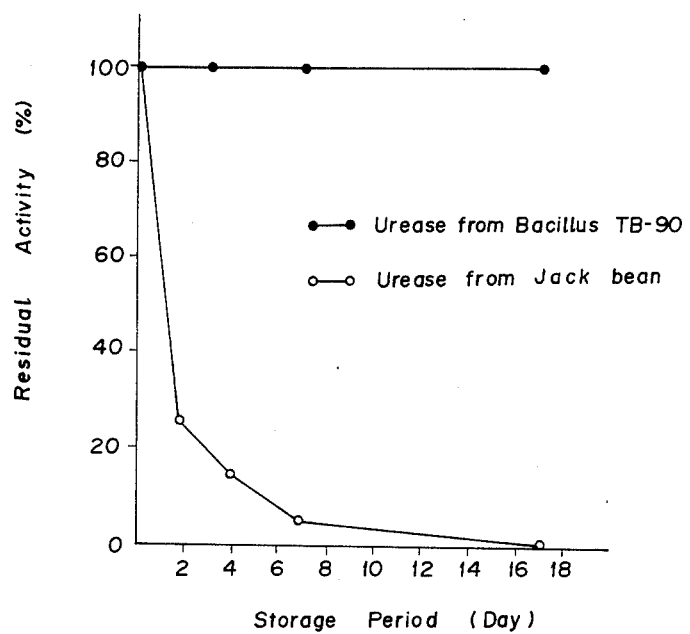
FIG. 5 is a graph showing the storage stability of the urease of the present invention.

The enzyme specimen was dissolved in a 50 mM phosphate buffer (pH 7.0) in a concentration of 180 mU/ml and maintained at 20° C. With a lapse of time, the residual activity was measured by the GlDH method. Changes in activity with incubation time are shown in FIG. 5 with the activity at the start of the experiment as 100. The urease derived from a jack bean as a control quickly lost its activity, whereas the urease derived from Strain TB-90 fully maintained its activity. Thus the usefullness of the present enzyme is apparent.

(7) Substrate Specificity

Using compounds having a structure similar to that of urea in place of the urea, the activity of the present enzyme onto the compounds was measured by the GlDH method. The results are shown in Table 1.

TABLE 1

Action of the Present Enzyme onto Substances having Structure similar to that of Urea

| Substrates | Final Concentration (mM) | Relative Activity (%) |
| --- | --- | --- |
| Urea | 2 | 100 |
| Acetoamide | 2 | 0 |
| Hydroxyurea | 2 | 0 |
| Semicarbazide | 2 | 0 |
| Salicylamide | 2 | 0 |
| Allantoin | 2 | 3 |
| Allantoic acid | 2 | 93 |
| Hydantoin | 2 | 0 |
| Biuret | 2 | 42 |
| Asparagine | 2 | 0 |

(8) Inhibitor

In a 50 mM phosphate buffer (pH 8.5) were dissolved 1 mM (as a final concentration) of each metal chloride and 100 mM of urea, and the resulting solution was maintained at a constant temperature of 37° C. Then 3.6 mU/ml (as a final concentration) of the enzyme specimen was added to the solution and reacted therewith for 15 minutes. Ammonia formed during this reaction was measured by the indophenol method. Magnesium, calcium, strontium, barium, aluminum, tin, lead, silver, manganese, iron (II), iron (III), sodium, potassium and lithium did little inhibit the present enzyme or activated the present enzyme. On the other hand, copper, zinc and mercury seriously inhibited the enzyme activity. Thus the inhibition test was performed changing the amount of such a metal added. The results are shown in Table 2.

TABLE 2

Inhibition by Metal Ions

| Metal Ion | Final Concentration (mM) | Relative Activity (%) |
| --- | --- | --- |
| — | — | 100 |
| Copper | 0.1 | 13 |
|  | 0.01 | 54 |
| Zinc | 0.1 | 50 |
| Mercury | 0.01 | 13.5 |
|  | 0.001 | 50 |

(9) Molecular Weight

The molecular weight as determined by the gel filtration method using Sephadex G-200 was about 240,000.

(10) Km Value

The Km value as determined under the conditions of the aforementioned GlDH method was about 0.3 mM for urea.

The present enzyme was sufficiently satisfactorily purified for the purpose of practical use, but has not yet been crystallized as a single enzyme protein. For this reason, the elemental analytical values, crystal structure and so forth of the present enzyme have not been clarified.

The urease of the present invention is excellent in stability. The storage stability as defined in (6) above of the present enzyme was compared with that of the urease derived from a jack bean in FIG. 5. In view of the fact that when the urease produced by the mesophilic Bacillus (Japanese Patent Kokai Koho No. 17987/1984) is stored at 5° C. for 4 days, its activity dropped to 70-75% of the original activity, it can be seen that the urease of the present invention is useful. When the urease of the present invention was stored at 5° C., no decrease in activity was observed for 3 months at least.

Since the urease of the present invention has a smaller Km value, it can be incorporated in artifical kidneys and can be utilized as a clinical analysis reagent for the quantitative determination of urea in the serum.

The enzyme urease of the present invention is greatly excellent in stability because it is derived from a thermophilic microorganism. Moreover it possesses properties that the Km value is small. Accordingly such annoyance as addition of a special stabilizer and low temperature storage as encountered in using the conventional urease derived from a jack bean as various products such as in artificial kidneys and a clinical analysis reagent can be greatly decreased. Moreover since the Km value is small, the amount of the present enzyme used can be markedly decreased. This is one of the advantages of the present invention. The preparation of the present enzyme can be accomplished efficiently in a short time because thermophilic microorganisms are used.

The present invention is described below in greater detail with reference to the following example.

EXAMPLE

As the seed culture, Strain TB-90 (FERM BP-795) was used.

In a large-sized test tube was placed 10 milliliter (ml) of a seed culture medium (pH 6.5) consisting of 1 gram per deciliter (g/dl) of glucose, 1 g/dl of yeast extract, 1 g/dl of peptone, 1 g/dl of $KH_2PO_4$, 1 g/dl of $K_2HPO_4$, 0.5 g/dl of $MgSO_4.7H_2O$ and tap water. After sterilization at 121° C. for 15 minutes, a platinum spoonful of the above seed culture was inoculated on the above medium and cultivated at 55° C. for 6 hours with shaking (350 strokes per minute).

Thirty milliliters of the above culture was added to 1.5 liters (l) of a production medium (3 g/dl glucose, 1 g/dl yeast extract, 0.5 g/dl peptone, 4 g/dl uric acid, 1 g/dl $KH_2PO_4$, 0.5 g/dl $MgSO_4.7H_2O$, 0.5 g/dl soy bean oil, and tap water) in a 5 liter-volume jar fermentator and then cultivated for 13 hours under conditions of temperature 55° C., number of revolution 300 rpm, and aeration amount 1 liter per liter medium (l/l medium) per minute.

At the end of the cultivation, Triton X-100 was added to the above fermentation broth in a final concentration of 0.1%, and urease was extracted at 7°-8° C. overnight. The extract thus obtained was subjected to centrifugal separation (10,000 G for 15 minutes) to obtain a supernatant liquid. The urease activity of the supernatant liquid was 20 U/ml (supernatant liquid 1.3 liters, total activity 26,000 U).

This supernatant liquid was concentrated with Amicon Hollow Fiber Cartiridge (H10P10-20 25) and further replaced with a 10 mM phosphate buffer (pH 6.0) (final liquid amount, 200 ml). To this concentrated liquid was added DEAE Toyopearl 650 M (Type C1), and they were stirred at room temperature for 30 minutes. Then, on a glass filter, an unabsorbed portion was removed by washing with a 10 mM phosphate buffer (pH 6.0). This resin absorbed urease was repeatedly washed until the absorption of ultraviolet rays (280 nm) could not be detected in washings, and then packed in a column having a diameter of 2.5 centimeters (cm).

Recovery of the enzyme was performed by the linear concentration gradient elution using 500 ml of a 10 mM phosphate buffer (pH 6.0) and a solution prepared by adding sodium chloride in the amount corresponding to 0.2 M to the above buffer. Urease was eluted in 0.15 M of sodium chloride.

To this fraction was added sodium sulfate in an amount that the total amount was 1 M and dissolved therein. This solution was passed through a column (diameter: 2.5 cm; effective length: 10 cm) of Butyl Toyo Pearl 650C which had been previously equilibrated with a 10 mM phosphate buffer (pH 7.0) containing 1 M sodium sulfate to thereby make the enzyme adsorbed thereon. The resin was washed by passing the solution until the absorption of ultraviolet ray (280 nm) in a 10 mM phosphate buffer containing 1 M sodium sulfate could not be detected. Then the elution was carried out with linearly decreasing the sodium sulfate concentration.

Urease fractions were collected and concentrated by the ultra filtration system (Mini Module MM-3 by Asahi Kasei Co., Ltd.) (about 2 ml). This concentrate was subjected to gel filtration using a column (diameter: 2.5 cm; effective length: 70 cm) packed with Toyo Pearl HW-55F which had been equilibrated with a 10 mM phosphate buffer (pH 7.0) to thereby obtain urease. This fraction was freeze-dried to obtain a purified urease powder (specific activity 30 U/mg protein). The ratio of active recovery from the extract of the fermentation broth was 40%. Unless otherwise specified, this purification process was carried out at a room temperature. The properties of the enzyme thus obtained were the same as described above.

What is claimed is:

1. Urease having an action of hydrolyzing urea and having the following properties:
    (a) stable at pH of from 5.8 to 8.0
    (b) stable at a temperature of from 20° to 56° C.
    (c) molecular weight: about 240,000 as determined by gel filtration method using Sephadex G-200 and
    (d) Km value: about 0.3 mM at pH 8.0.

2. A process for preparing urease having an action of hydrolyzing urea and being stable at pH of from 5.8 to 8.0; stable at a temperature of from 20° to 56° C. having a molecular weight of about 240,00 as determined by gel filtration method using Sephadex G-200 and a Km value of about 0.3 mM at pH 8.0 comprising
    cultivating a thermophilic microorganism designated Bacillus Sp. TB-90 (FERM BP-795 ) or a mutant thereof in a nutrient medium to produce the urease; and recovering the urease.

3. Urease produced by the process of claim 2.

* * * * *

UNITED STATES PATENT AND TRADEMARK OFFICE
CERTIFICATE OF CORRECTION

PATENT NO. : 4,753,882
DATED : June 28, 1988
INVENTOR(S) : TAKASHIO et al It is certified that error appears in the above-identified patent and that said Letters Patent is hereby corrected as shown below:

Column 10, line 17 (Claim 2):

Change "240,00" to --240,000--.

Signed and Sealed this

Eleventh Day of August, 1992

*Attest:*

DOUGLAS B. COMER

*Attesting Officer*     *Acting Commissioner of Patents and Trademarks*